(12) United States Patent
Honguh

(10) Patent No.: US 7,796,253 B2
(45) Date of Patent: Sep. 14, 2010

(54) IMAGE FORMING APPARATUS FOR FORMING IMAGE ON RECORD MEDIUM

(75) Inventor: Yoshinori Honguh, Yokohama (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 586 days.

(21) Appl. No.: 11/735,719

(22) Filed: Apr. 16, 2007

(65) Prior Publication Data
US 2008/0252887 A1 Oct. 16, 2008

(51) Int. Cl.
*G01N 21/00* (2006.01)
(52) U.S. Cl. ...................... 356/337; 356/338
(58) Field of Classification Search ......... 356/432–442, 356/337–342
See application file for complete search history.

(56) References Cited

U.S. PATENT DOCUMENTS 6,819,411 B1 * 11/2004 Sharpe et al. ............... 356/72
2006/0244965 A1 11/2006 Ichijo

FOREIGN PATENT DOCUMENTS

WO 2004025279 3/2004

* cited by examiner

*Primary Examiner*—Michael P Stafira
(74) *Attorney, Agent, or Firm*—Turocy & Watson, LLP

(57) ABSTRACT

A particle detecting device including a light source light reflector to reflect a laser light to make it intersect an observed light path of a light detector plural times at different positions, or a scattered light reflector to reflect the observed light path of the light detector to make it intersect the laser light plural times at different positions is installed on a side of a printed surface of a record medium in the inside of an image forming apparatus.

14 Claims, 11 Drawing Sheets

MODULATING
SIGNAL

MODULATING
SIGNAL

OUTPUT
SIGNAL

REFLECTION BY MOVING MIRROR

CYLINDRICAL LENS

DIFFRACTION GRATING

IMAGE FORMING APPARATUS FOR FORMING IMAGE ON RECORD MEDIUM

BACKGROUND OF THE INVENTION

1. Field of the Invention

The present invention relates to an image forming apparatus for forming an image on a record medium, which includes a particle detecting device to detect particles by irradiating a light beam to particles existing in a gas, liquid or transparent solid and by detecting a scattered light.

2. Description of the Related Art

Hitherto, a device which irradiates a light such as a laser beam to particles and detects the particles by detecting a scattered light thereof has been developed. As particles of detection objects, there are various particles including a solid particle, a microorganism and a molecular aggregate.

Besides, in recent years, an image forming apparatus such as a copier becomes precise, and in order to perform excellent image formation, when the amount of minute paper powder in the image forming apparatus becomes a specific amount or more, it becomes necessary to remove the powder. Thus, the development of a particle detecting device to detect the minute paper powder in the image forming apparatus has been demanded.

In the related art, there is proposed a technique in which a laser beam is reciprocated so that particle detection accuracy is raised (for example, International Publication No. WO2004/025279).

This is such that a reflecting film is provided on a nonlinear optical crystal through which a light beam is transmitted, a reflecting mirror is provided in a light path of the light beam whose wavelength is converted, and the light beam whose wavelength is converted is reciprocated between the reflecting film and the reflecting mirror, so that a light with higher energy density than a light irradiated from a light source can be obtained.

However, in this technique, since the light beam to be irradiated to the particles is one straight line, the range where the light can be irradiated is limited. Further, the number of particles to which the light beam is irradiated is not increased as compared with the case where the light beam is not reciprocated. Accordingly, there is a problem that this is not effective in the object of detecting the presence or absence of particles existing in an area to be observed or the number thereof with high accuracy.

BRIEF SUMMARY OF THE INVENTION

It is an object of the present invention to provide an image forming apparatus including a particle detecting device which includes a reflector to reflect a laser light or an observed light path for observing the laser light scattered by a particle, so that the laser light and the observed light path intersect each other plural times at different positions.

In an aspect of the present invention, an image forming apparatus for forming an image on a record medium includes
  a particle detecting device including
    a laser light source to irradiate a laser light,
    a light detector to detect the laser light scattered by a particle, and
    a light source light reflector to reflect the laser light to make it intersect an observed light path of the light detector plural times at different positions, or
    a scattered light reflector to reflect the observed light path of the light detector to make it intersect the laser light plural times at different positions.

DETAILED DESCRIPTION OF THE INVENTION

Throughout this description, the embodiments and examples shown should be considered as exemplars, rather than limitations on the apparatus and methods of the present invention.

Hereinafter, an embodiment of an image forming apparatus for forming an image on a record medium according to the invention will be described in detail by use of the drawings.

<Particle Detecting Device>

First, a particle detecting device will be described.

First Embodiment

Figure 1:
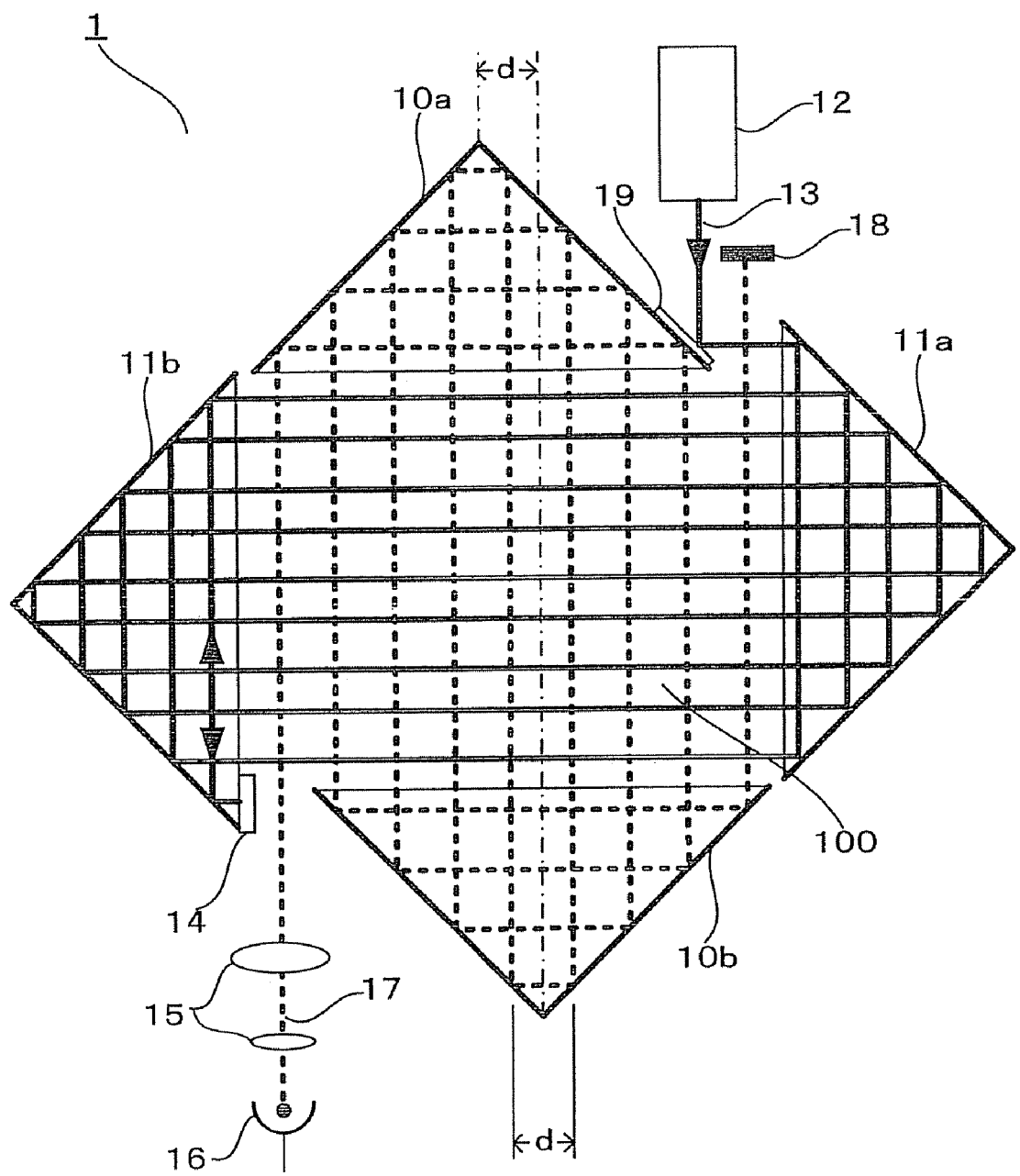
FIG. 1 is a structural view showing the outline of a particle detecting device of a first embodiment.

A rough structure of a particle detecting device 1 of a first embodiment will be described with reference to FIG. 1. This embodiment is characterized by constructing and arranging light source light reflectors 11a and 11b or scattered light reflector 10a and 10b to reflect a laser light 13 or an observed light path 17 so that the laser light and the observed light path intersect each other plural times at different positions.

The particle detecting device 1 of this embodiment includes a laser light source 12 to irradiate a laser light, a light detector 16 to detect the laser light scattered by a particle and condensed by a lens 15, the scattered light reflectors 10a and 10b to reflect the observed light path 17 through which the light detector 16 observes the laser light 13 scattered by the particle, and the light source light reflectors 11a and 11b to reflect the laser light 13.

The light detector 16 has only to have a function of converting a light into an electric signal, and its kind can be suitably selected.

The scattered light reflectors 10a and 10b, and the light source light reflectors 11a and 11b may be constructed such that either one pair are provided, or both pairs are provided. Besides, a component to reflect a laser light is used for the scattered light reflectors 10a and 10b and the light source light reflectors 11a and 11b. For example, a mirror or a prism made of a transparent solid different from air in refractive index, such as glass, crystal or transparent resin, can be used.

A black body 18 to absorb the scattered light traveling in the direction opposite to the light detector 16 may be provided at the terminal end of the observed light path 17. A total reflection mirror 14 may be provided at the terminal end of the light path of the laser light 13.

The shapes of the scattered light reflectors 10a and 10b and the light source light reflectors 11a and 11b of the embodiment can be formed as described below. In the case where a prism is used, one having the shape of a triangular prism with the bottom surface of a rectangular equilateral triangle is used. In this case, lateral surfaces including sides containing the right angle of the bottom surface, that is, in FIG. 1, lateral surfaces including the sides shown to be thick among the sides of the scattered light reflectors 10a and 10b and the light source reflectors 11a and 11b become the reflecting surfaces.

In the case where a mirror is used, two mirrors having equal widths are arranged at the right angle. In this case, the lateral surfaces including the sides containing the right angle of the bottom surface, that is, the lateral surfaces including the sides shown to be thick in FIG. 1 among the sides of the scattered light reflectors 10a and 10b and the light source light reflectors 11a and 11b are made the mirrors.

The arrangement of the scattered light reflectors 10a and 10b and the light source light reflectors 11a and 11b in this embodiment can be made as described below. When intervals between reflection points of the observed light path 17 on the reflecting surfaces of the scattered light reflectors 10a and 10b are equal to one another, the minimum width between the reciprocating light paths is made d. The pair of the scattered light reflectors 10a and 10b are arranged to be opposite to each other across an observation area 100 which is an area where the laser light 13 is irradiated to particles, so that surfaces including the bases of the bottom surfaces become parallel to each other. At this time, the centers of the pair of the scattered light reflectors 10a and 10b, here, the apexes of the bottom surfaces are positioned to be shifted by d in the length direction of the base of the bottom surface as indicated by alternate long and short dash lines.

Next, the pair of the light source light reflectors 11a and 11b are arranged to be opposite to each other across the observation area 100, so that the surfaces including the bases of the bottom surfaces become parallel to each other. When intervals of reflection points of the laser light 13 on the reflecting surfaces of the light source light reflectors 11a and 11b are equal to one another, the minimum width between the reciprocating light paths is made d. At this time, the centers of the pair of the light source light reflectors 11a and 11b, here, the apexes of the bottom surfaces are arranged to be shifted by d in the length direction of the base of the bottom surface.

Further, the scattered light reflectors 10a and 10b and the light source light reflectors 11a and 11b are arranged so that the laser light 13 intersects the observed light path 17 plural times at different positions. For example, when the light paths of the laser light 13 in the observation area 100 are on the same plane, and the observed light paths 17 in the observation area 100 are on the same plane, the scattered light reflectors 10a and 10b and the light source light reflectors 11a and 11b are arranged so that these planes become the same plane.

Next, the light path of the laser light 13 will be described. The laser light 13 irradiated from the laser light source 12 is reflected by a mirror 19, is incident on the first light source light reflector 11a, is reflected by the reflecting surface of the reflector, passes through the observation area 100, and is incident on the second light source light reflector 11b. The laser light 13 incident on the second light source light reflector 11b is reflected by the reflecting surface of the reflector, passes through the observation area 100, and is again incident on the first light source light reflector 11a. When this is repeated, since the apexes are shifted from each other by d, the incident position of the laser light 13 on the light source light reflectors 11a and 11b is sequentially moved, and finally reaches the total reflection mirror 14. The laser light 13 is reflected by the total reflection mirror 14, and returns along the light path along which it has come. As stated above, plural light paths of the laser light 13 are produced in the observation area 100.

Next, the observed light path 17 will be described in sequence from the light detector 16. The observed light path 17 is incident on the first scattered light reflector 10a, is reflected by the reflecting surface of the reflector, passes through the observation area 100, and is incident on the second scattered light reflector 10b. The observed light path 17 incident on the second scattered light reflector 10b is reflected by the reflecting surface of the reflector, passes through the observation area 100, and is again incident on the first scattered light reflector 10a. When this is repeated, since the apexes are shifted from each other by d, the incident position of the observed light path 17 is sequentially moved, and finally reaches the blackbody 18. As stated above, plural light paths of the observed light path are produced in the observation area 100.

Next, the detection of the laser light 13 scattered by a particle will be described. The particle in the observation area 100 scatters the laser light 13. Here, as described before, the laser light 13 intersects the observed light path 17 plural times at different positions. The scattered light scattered by the particle in the intersection portion advances along the observed light path 17, is condensed by the lens 15, and reaches the light detector 16. That the amount of detected light is high means that the number of particles existing in the observation area 100 is large.

Incidentally, in the case where this embodiment is used for a device to detect paper particles in an apparatus handling paper, such as an image forming apparatus, the structure can be made such that a blower such as a fan is provided, the air containing paper particles to be detected is made to flow into the observation area 100 by this blower, and the detection is performed.

In the case where this embodiment is used for a device to detect particles in a liquid, the structure can be made such that a sample is contained in a transparent container and is inserted into the observation area, or a transport apparatus such as a pump is provided, and a sample is made to pass through the observation area 100 through a transparent pipe, so that the detection of particles is performed.

In the case where this embodiment is used for a device to detect particles in a transparent solid, the structure can be made such that a sample is inserted in the observation area so that the detection of particles is performed.

The wavelength of the irradiated laser light 13 can be suitably selected according to the diameter of a particle to be detected.

Incidentally, in this embodiment, although the description has been made using the example in which the light paths of the laser light 13 and the observed light paths 17 are respectively parallel to each other, it is not necessary that these are respectively parallel, and they may be radial or may intersect each other.

As described above, in the embodiment, there are provided the light source light reflectors 11a and 11b or the scattered light reflectors 10a and 10b to reflect the laser light 13 or the observed light path 17 so that the laser light 13 and the observed light path 17 intersect plural times at different positions. Thus, as compared with the particle detecting device of the related art in which the laser light 13 and the observed light path intersect at only one place, there is an effect that the particle can be detected with high accuracy by the factor of the number of times of intersection.

Second Embodiment

Next, a second embodiment will be described. This embodiment is characterized by providing a light source light reflector to reflect a laser light in a first direction and in a direction different from the first direction, so that the laser light intersects an observed light path of a light detector plural times at different positions.

Figure 2:
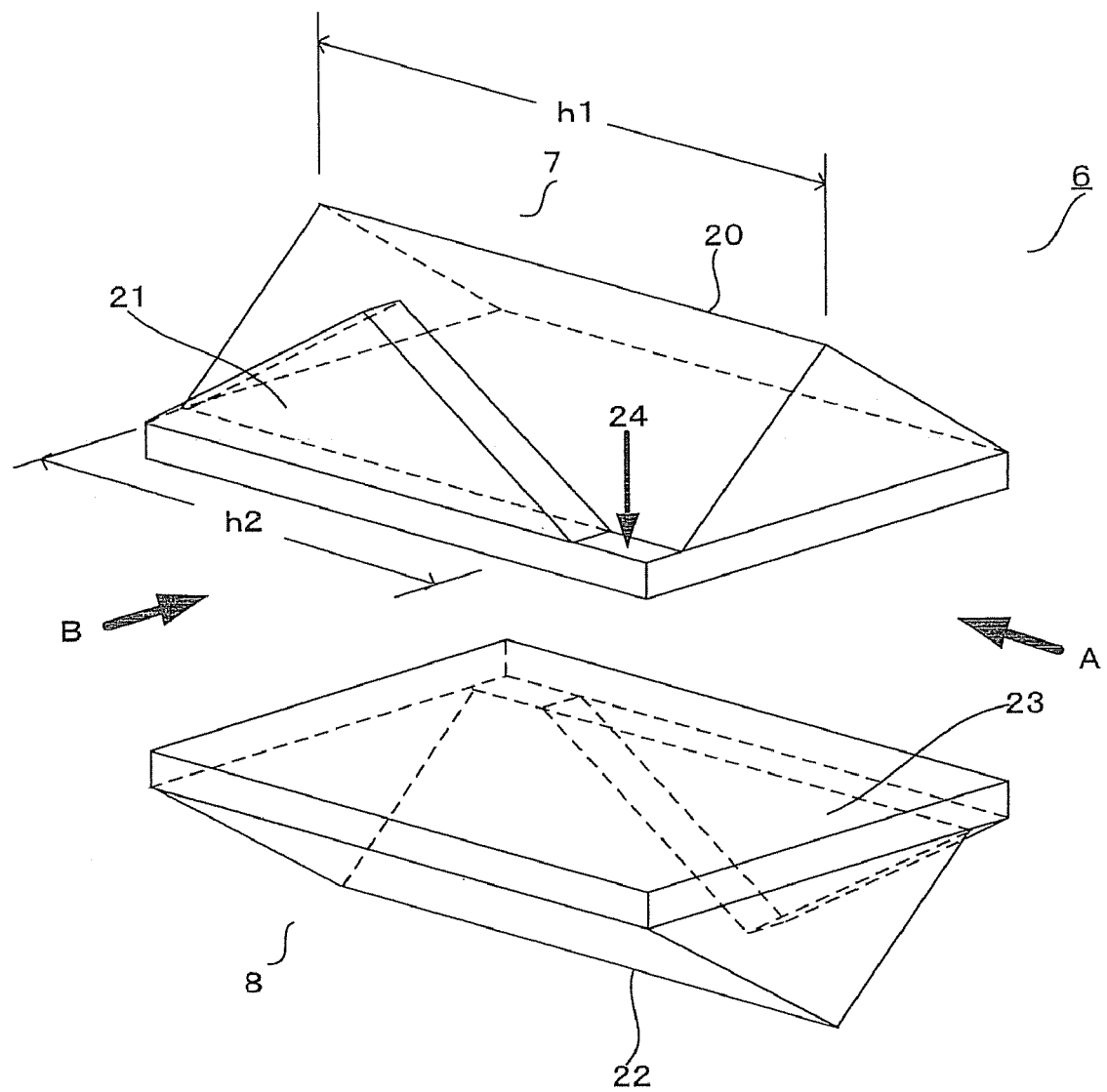
FIG. 2 is a perspective view of a light source light reflector of a particle detecting device of a second embodiment.

A rough structure of a particle detecting device 2 of the second embodiment will be described with reference to FIGS. 2 to 4. FIG. 2 is a perspective view of a three-dimensional light source light reflector 6 of this embodiment. The three-dimensional light source light reflector 6 of this embodiment includes a first three-dimensional light source light reflector 7 and a second three-dimensional light source light reflector 8 arranged to be opposite thereto across an observation area 100.

The first three-dimensional light source light reflector 7 includes a first reflecting unit 20 which is a triangular prism with a bottom surface of a rectangular equilateral triangle and is arranged such that a surface including the hypotenuse of the bottom surface faces the observation area 100, and a second reflecting unit 21 which is a triangular prism with a bottom surface of a rectangular equilateral triangle, and is arranged such that its bottom surface faces a lateral surface of the first reflecting unit 20, and a surface including the hypotenuse of the bottom surface faces the observation area 100.

Incidentally, a height h1 of the first reflecting unit 20 is made longer than the hypotenuse h2 of the second reflecting unit 21. By this, an area on which a laser light 24 is incident is ensured.

The second three-dimensional light source light reflector 8 includes a first reflecting unit 22 which is a triangular prism with a bottom surface of a rectangular equilateral triangle, and is arranged such that a surface including the hypotenuse of the bottom surface faces the observation area 100, and a second reflecting unit 23 which is a triangular prism with a bottom surface of a rectangular equilateral triangle, and is arranged such that its bottom surface faces a lateral surface of the first reflecting unit 22, and a surface including the hypotenuse of the bottom surface faces the observation area 100.

Incidentally, the height of the first reflecting unit 22 is made longer than the hypotenuse of the bottom surface of the second reflecting unit 23. By this, a terminal end to which the laser light 24 reaches is ensured. The structure may be made such that a total reflection mirror is provided at the terminal end, and the laser light 24 returns.

As the three-dimensional light source light reflector 6, a device to reflect a laser light is used. For example, a mirror or a prism made of a transparent solid different from air in refractive index, such as glass, crystal or transparent resin, can be used.

Figure 3:
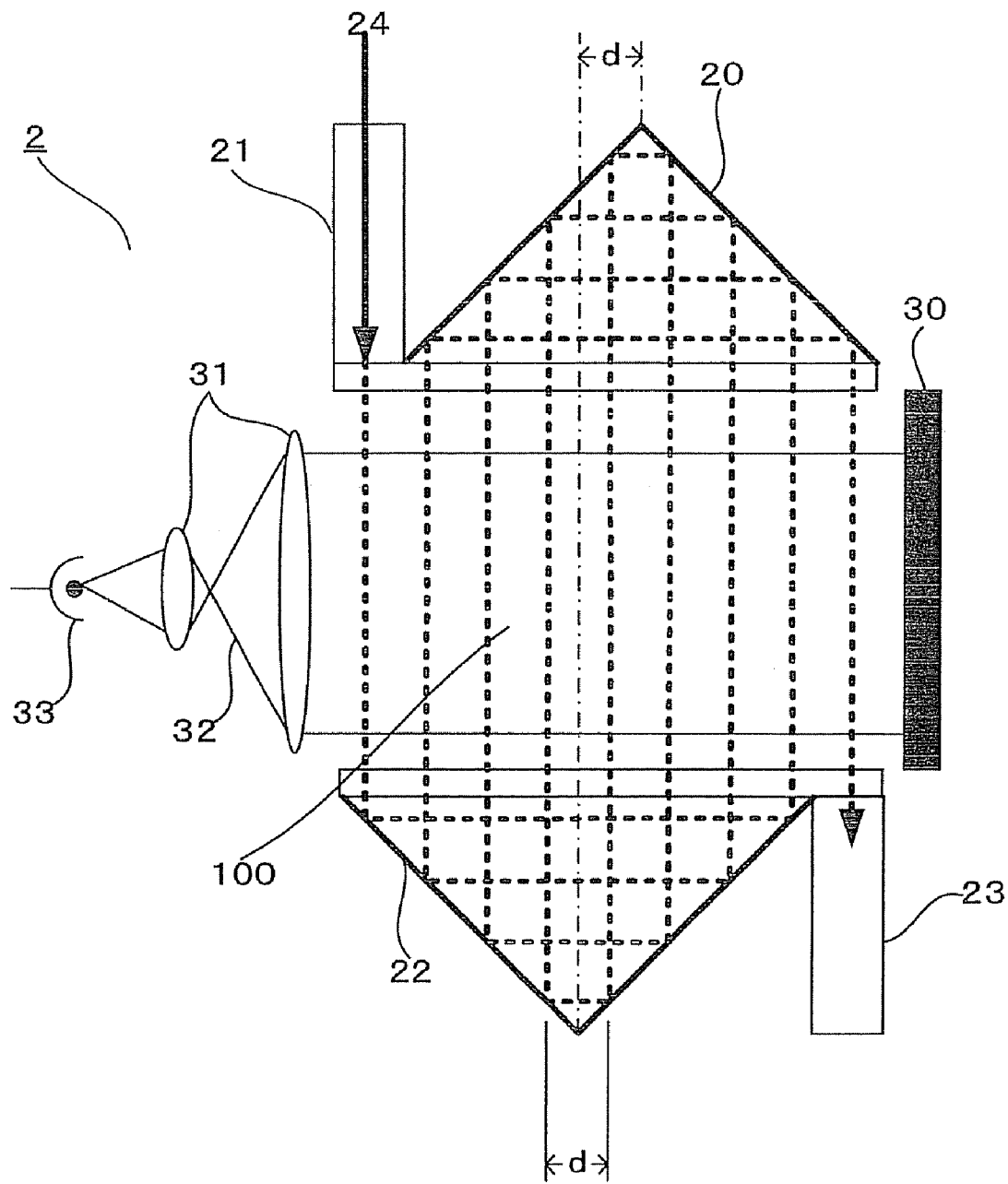
FIG. 3 is a view of the particle detecting device of the second embodiment seen from a direction A in FIG. 2.

FIG. 3 is a view of the particle detecting device 2 of this embodiment seen in the direction of an arrow A of FIG. 2. The particle detecting device 2 of this embodiment includes the three-dimensional light source light reflector 6, a not-shown laser light source to irradiate the laser light 24, and a light detector 33 to detect the laser light scattered by a particle and condensed by a lens 31.

An observed light path of the light detector 33 can also be formed by using the scattered light reflectors to reflect the observed light path to make it intersect the laser light plural times at different positions, which are described in the first embodiment. Besides, it can also be formed by further providing an after-mentioned pair of three-dimensional light source light reflectors 6.

In this embodiment, a description will be made while using an example in which as shown in FIG. 3, an observation is made in a direction different from the light path of the laser light 24 in the observation area 100 and in one direction.

The light detector 33 has only to have a function of converting a light into an electric signal, and its kind can be suitably selected.

The arrangement of the first reflecting units 20 and 22 and the second reflecting units 21 and 23 in this embodiment can be constructed, for example, as described below. When intervals of reflection points of the laser light 24 on the reflecting surface are equal to each other, the minimum width between the reciprocating light paths is made d. The pair of the first reflecting units 20 and 22 are arranged to be opposite to each other across the observation area 100 where the laser light 13 is irradiated to a particle, so that the surfaces including the bases of the bottom surfaces become parallel to each other. At this time, the centers of the first reflecting units 20 and 22, here, the apexes of the bottom surfaces are positioned to be shifted from each other by d in the length direction of the base of the bottom surface as indicated by alternate long and short dash lines.

The pair of the second reflecting units 21 and 23 are arranged at the shifted positions. As a result, as shown in FIG. 3, in the first three-dimensional light source light reflector 7, when the first reflecting unit 20 is positioned at the right and the second reflecting unit 21 is positioned at the left, in the second three-dimensional light source light reflector 8, the first reflecting unit 22 is positioned at the left and the second reflecting unit 23 is positioned at the right.

Figure 4:
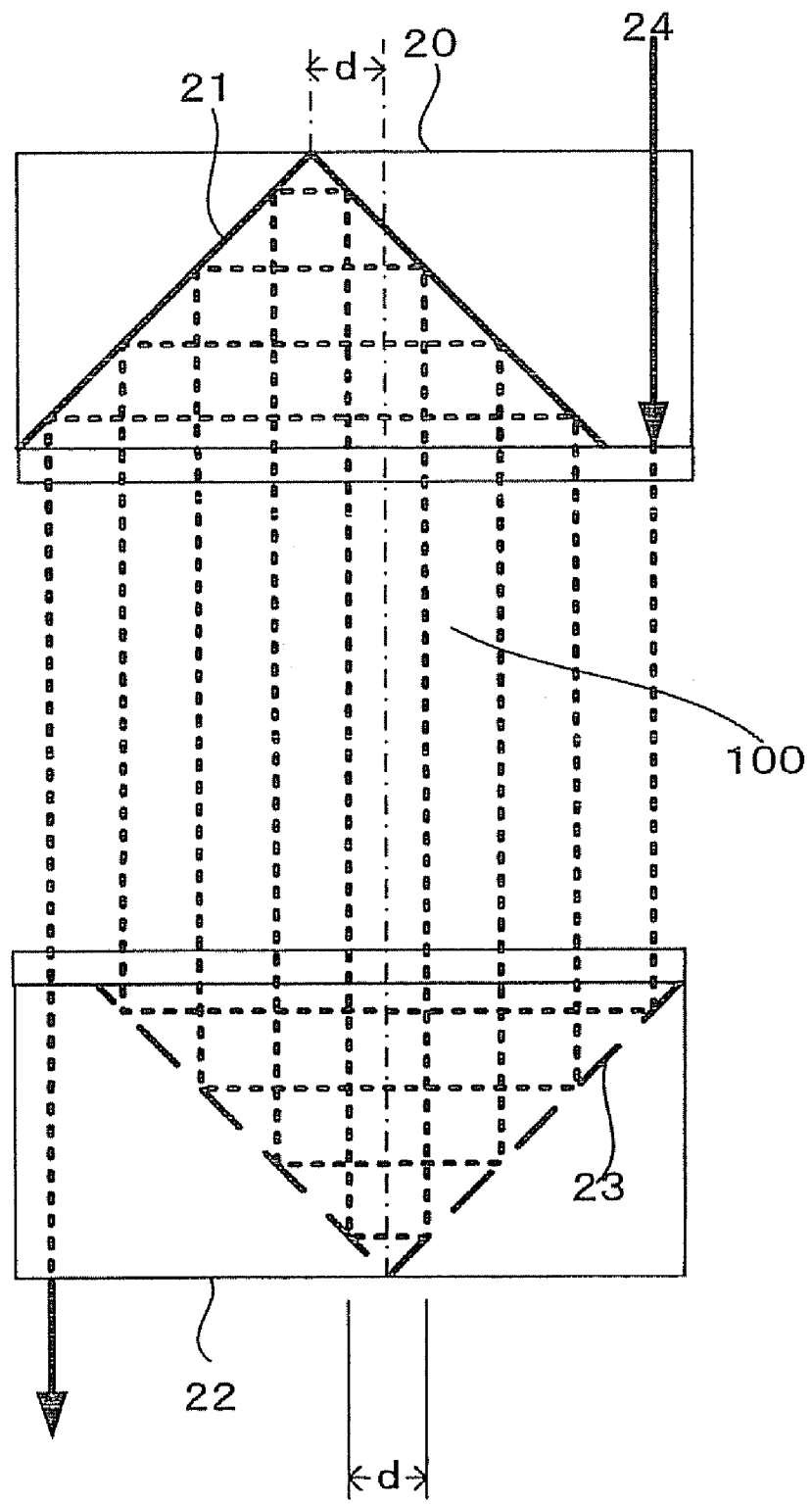
FIG. 4 is a view of the particle detecting device of the second embodiment seen from a direction B in FIG. 2.

FIG. 4 is a view of the particle detecting device 2 of this embodiment seen in the direction of an arrow B of FIG. 2. The pair of the second reflecting units 21 and 23 are arranged to be opposite to each other across the area where the laser light 13 is irradiated to a particle, so that the surfaces including the bases of the bottom surfaces become parallel to each other. At this time, the centers of the reflecting units 21 and 23, here, the apexes of the bottom surfaces are positioned to be shifted from each other by d in the length direction of the base of the bottom surface as indicated by alternate long and short dash lines.

Further, the three-dimensional light source light reflector 6 and the light detector 33 are arranged so that the laser light 24 intersects the observed light path 32 plural times at different positions.

Next, the light path of the laser light 24 will be described. As shown in FIG. 3, the laser light 24 incident from the first three-dimensional light source light reflector 7 is reflected by the first reflecting unit 22 of the second three-dimensional light source light reflector 8, passes through the observation area 100, and is incident on the first reflecting unit 20 of the first three-dimensional light source light reflector 7. The laser light 24 incident on the first reflecting unit 20 of the first three-dimensional light source light reflector 7 is reflected by the reflecting surface of the reflecting unit, passes through the observation area 100, and is again incident on the first reflecting unit 22 of the second three-dimensional light source light reflector 8. When this is repeated, since the apexes of the first reflecting units 20 and 22 is shifted by d, the incident position of the laser light 24 on the first reflecting units 20 and 22 is sequentially moved, and finally reaches the second reflecting unit 23 of the second three-dimensional light source light reflector 8.

As shown in FIG. 4, the laser light 24 having reached the second reflecting unit 23 of the second three-dimensional light source light reflector 8 is reflected by the reflecting surface of the reflecting unit, and is again incident on the first reflecting unit 20 of the first three-dimensional light source light reflector 7. The incident light advances so as to go back along the foregoing path shown in FIG. 3, and finally reaches the second reflecting unit 21 of the first three-dimensional light source light reflector 7.

As shown in FIG. 4, the laser light 24 having reached the second reflecting unit 21 of the first three-dimensional light source light reflector 7 is reflected by the reflecting surface of the reflecting unit and is again incident on the first reflecting unit 22 of the second three-dimensional light source light reflector 8. When this is repeated, since the apexes of the second reflecting units 21 and 23 are shifted by d, the incident position of the laser light 24 on the second reflecting units 21 and 23 is sequentially shifted, and finally reaches the foregoing terminal end.

Next, the detection of the laser light 24 scattered by a particle will be described. The particle in the observation area 100 scatters the laser light 24. Here, as described before, the laser light 24 intersects the observed light path 32 plural times at different positions. The scattered light scattered by the particle in the intersection portion advances along the observed light path 32, is condensed by the lens 31 and reaches the light detector 33. That the amount of detected light is high means that the number of particles existing in the observation area 100 is large.

As stated above, in this embodiment, the first reflecting units 20 and 22 reflect the laser light 24 in the first direction, and the second reflecting units 21 and 23 reflect the laser light 24 in the direction different from the first direction.

Incidentally, in this embodiment, although the description has been made while using the example in which the light paths of the laser light 24 become parallel to each other, it is not necessary that these are parallel, and they may be radial or intersect each other.

The shapes of the first three-dimensional light source light reflector 7 and the second three-dimensional light source light reflector 8 are not limited to the foregoing shapes, and polygons of various shapes can be used.

As described above, in this embodiment, there is provided the three-dimensional light source light reflector 6 to reflect the laser light 24 in the first direction and the direction different from the first direction, so that it intersects the observed light path 32 of the light detector 33 plural times at different positions. Thus, the number of positions where the laser light 24 intersects the observed light path 32 is increased, and there is an effect that particle detection with higher accuracy becomes possible.

Third Embodiment

Next, a third embodiment will be described. This embodiment is characterized in that the sectional shapes of scattered light reflectors 53a and 53b and light source light reflectors 54a and 54b are made polygonal.

Figure 5:
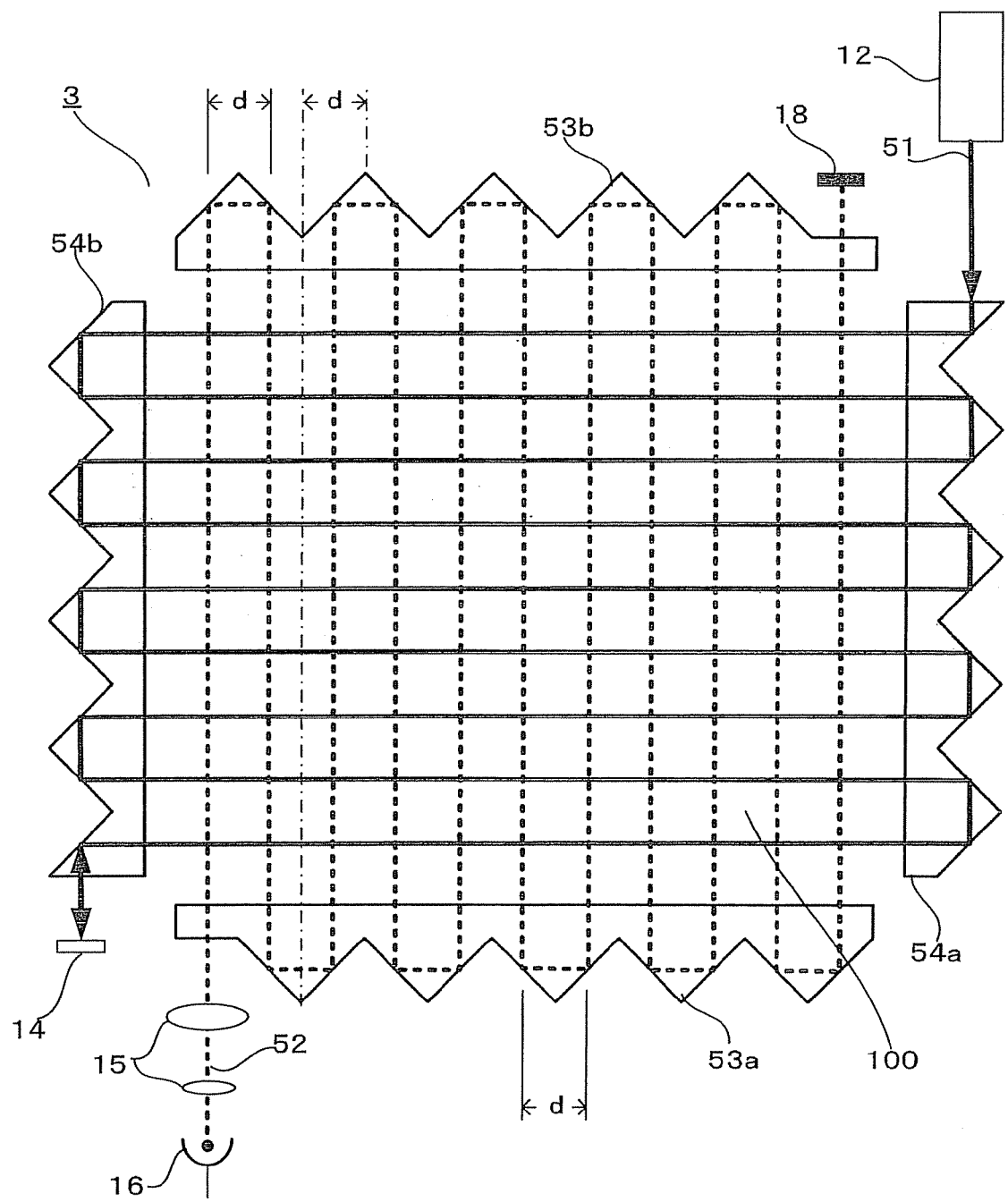
FIG. 5 is a structural view showing the outline of a particle detecting device of a third embodiment.

A rough structure of a particle detecting device 3 of the third embodiment will be described with reference to FIG. 5. The particle detecting device 3 of this embodiment includes a laser light source 12 to irradiate a laser light, a light detector 16 to detect the laser light scattered by a particle and condensed by a lens 15, the scattered light reflectors 53a and 53b to reflect an observed light path 52 through which the light detector 16 observes a laser light 51 scattered by a particle, and light source light reflectors 54a and 54b to reflect the laser light 51.

The light detector 16 has only to have a function of converting a light into an electric signal, and its kind can be suitably selected.

The scattered light reflectors 53a and 53b and the light source light reflectors 54a and 54b may be constructed such that either one pair is provided or both pairs are provided. Besides, as the scattered light reflectors 53a and 53b and the light source light reflectors 54, a device to reflect a laser light is used. For example, a mirror or a prism made of a transparent solid different from air in refractive index, such as glass, crystal or transparent resin, can be used.

A black body 18 to absorb the scattered light traveling in the direction opposite to the light detector 16 may be provided at the terminal end of the observed light path 52. A total reflection mirror 14 may be provided at the terminal end of the light path of the laser light 51.

The shapes of the scattered light reflectors 53a and 53b and the light source light reflectors 54a and 54b in this embodiment can be formed, for example, as described below. In the case where a prism is used, a columnar body having a bottom surface as described below is used. First, rectangular equilateral triangles are arranged so that the hypotenuses are positioned on the same straight line. A rectangle having a side longer than the total length of these hypotenuses is arranged at these hypotenuses so that one end extrudes in the longitudinal direction. When the arrangement is made as stated above, the result becomes like the scattered light reflectors 53a and 53b and the light source light reflectors 54a and 54b shown in FIG. 5.

In the case where a mirror is used, the mirror is used on the lateral surface including two sides, which are equal to each other in length, of the rectangular equilateral triangle of the bottom surface of the foregoing columnar body.

The arrangement of the scattered light reflectors 53a and 53b and the light source light reflectors 54a and 54b in this embodiment can be constructed, for example, as described below. When intervals of reflection points of the observed light path 52 on the reflecting surfaces of the scattered light reflectors 53a and 53b are equal to each other, the width between the reciprocating light paths is made d. The pair of the scattered light reflectors 53a and 53b are arranged to be opposite to each other across the observation area 100, so that the surfaces including the sides opposite to the apexes of the equilateral triangles included on the bottom surfaces, that is, the surfaces without roughness become parallel to each other. At this time, the centers of the pair of the scattered light reflectors 53a and 53b, here, the apexes of the bottom surfaces are positioned to be shifted from each other by d in the length direction of the base of the bottom surface as indicated by alternate long and short dash lines.

Next, the pair of the light source light reflectors 54a and 54b are arranged to be opposite to each other across the observation area 100, so that the surfaces including the sides opposite to the apexes of the equilateral triangles included on the bottom surfaces, that is, the surfaces without roughness become parallel to each other. When intervals of reflection points of the laser light 51 on the reflecting surfaces of the light source light reflectors 54a and 54b are equal to each other, the minimum width between the reciprocating light paths is made d. At this time, the centers of the pair of the light source light reflectors 11, here, the apexes of the bottom surface are arranged to be shifted from each other by d in the length direction of the base of the bottom surface.

Further, the scattered light reflectors 53 and the light source light reflectors 54a and 54b are arranged so that the laser light 51 intersects the observed light path 52 plural times at different positions. For example, when the light paths of the laser light 51 in the observation area 100 are on the same plane, and the observed light paths 52 in the observation area 100 are on the same plane, the scattered light reflectors 53a and 53b and the light source light reflectors 54a and 54b are arranged so that these planes become the same plane.

Next, the light path of the laser light 51 will be described. The laser light 51 irradiated from the laser light source 12 is incident on the first light source light reflector 54a, is reflected by the reflecting surface of the reflector, passes through the observation area 100, and is incident on the second light source light reflector 54b. The laser light 51 incident on the second light source light reflector 54b is reflected by the reflecting surface of the reflector, passes through the observation area 100, and is again incident on the first light source light reflector 54a. When this is repeated, since the apexes are shifted by d, the incident position of the laser light 51 on the light source light reflectors 54a and 54b is sequentially moved, and finally reaches the total reflection mirror 14. The laser light 51 is reflected by the total reflection mirror 14, and returns along the light path along which it has come. As stated above, the plural light paths of the laser light 51 are produced in the observation area 100.

Next, the observed light path 52 will be described in sequence from the light detector 16. The observed light path 52 passes through the second scattered light reflector 53b, passes through the observation area 100, is incident on the first scattered light reflector 53a, is reflected by the reflecting surface of the reflector, passes through the observation area 100, and is incident on the second scattered light reflector 53b. The observed light path 52 incident on the second scattered light reflector 53b is reflected by the reflecting surface of the reflector, passes through the observation area 100, and is again incident on the first scattered light reflector 53a. When this is repeated, since the apexes are shifted by d, the incident position of the observed light path 52 is sequentially moved, and finally reaches the black body 18. As stated above, plural light paths of the observed light path are produced in the observation area 100.

Next, the detection of the laser light 51 scattered by a particle will be described. The particle in the observation area 100 scatters the laser light 51. Here, as stated before, the laser light 51 intersects the observed light path 52 plural times at different positions. The scattered light scattered by the particle in the intersection portion travels along the observed light path 52, is condensed by the lens 15, and reaches the light detector 16. That the amount of detected light is high means that the number of particles existing in the observation area 100 is large.

Incidentally, in this embodiment, although the description has been made while using the example in which the light paths of the laser light 51 and the observed light paths 52 respectively become parallel to each other, it is not necessary that they are parallel, and they may be radial or intersect each other.

Besides, the sectional shapes of the scattered light reflectors 53a and 53b and the light source light reflectors 54a and 54b have only to be polygonal, and the shapes are not limited.

As described above, in this embodiment, the sectional shapes of the scattered light reflectors 53a and 53b and the light source light reflector 54a and 54b are made polygonal. By this, the scattered light reflectors 53a and 53b and the light source light reflectors 54a and 54b are miniaturized, so that the particle detecting device 3 can also be miniaturized, and there is an effect that it can be contained in a narrow space, and the manufacture cost can be reduced.

Fourth Embodiment

Next, a fourth embodiment will be described. This embodiment is characterized in that a laser light 51 is modulated, a light synchronous with the modulation applied to the laser light 51, that is, the laser light 51 scattered by a particle is detected from the light incident on a light detector 16, so that the particle can be detected even if a light other than the laser light 51 exists in the observation area 100.

Figure 6:
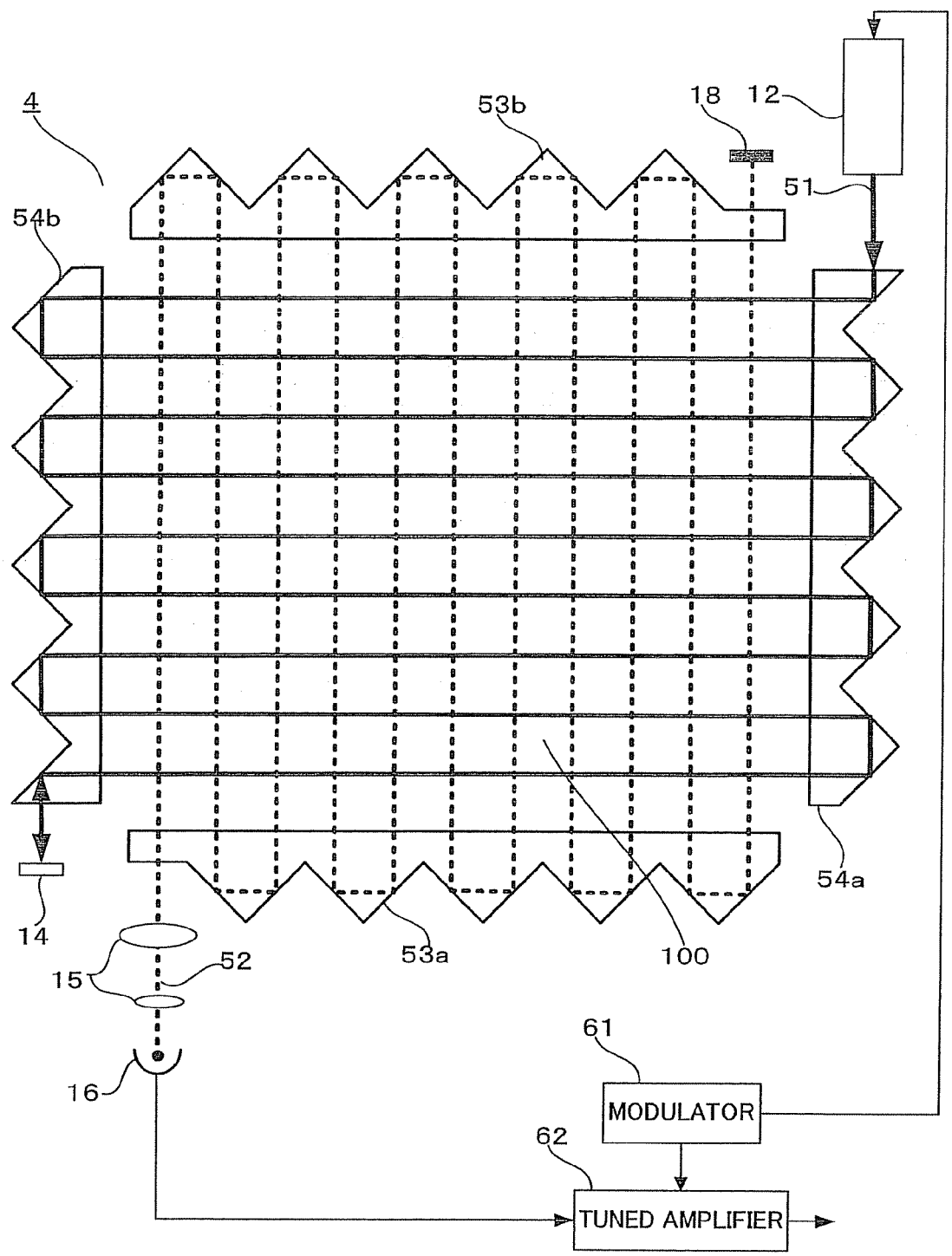
FIG. 6 is a structural view showing the outline of a particle detecting device of a fourth embodiment.

A rough structure of a particle detecting device 4 of the fourth embodiment will be described with reference to FIG. 6. Incidentally, this embodiment can be carried out in any of the particle detecting devices of the embodiments 1 to 3. Hereinafter, a description will be given to an example in which it is carried out in the third embodiment.

The particle detecting device 4 of the embodiment includes a laser light source 12 to irradiate a laser light, a light detector 16 to detect the laser light scattered by a particle and condensed by a lens 15, scattered light reflectors 53a and 53b to reflect an observed light path 52 through which the light detector 16 observes the laser light 51 scattered by a particle, light source light reflectors 54a and 54b to reflect the laser light 51, a modulator 61 to output a signal, which adds modulation to the laser light 51, to the laser light source 12 and an after-mentioned tuned amplifier 62, and the tuned amplifier 62 to receive an output signal obtained by converting the light detected by the light detector 16 into an electric signal, to amplify the output signal, and to extract a signal synchronous with the modulating signal.

The light detector 16 has only to have a function of converting a light to an electric signal, and its kind can be suitably selected.

As the modulator 61, for example, one to make the laser light 51 have a specific frequency, one to make the laser light 51 a periodic or random pulse, or the like can be used. The tuned amplifier 62 includes an amplifying device and a device to extract a tuning signal.

The scattered light reflectors 53a and 53b and the light source light reflectors 54a and 54b may be constructed such that either one pair is provided or both pairs are provided. Besides, as the scattered light reflectors 53a and 53b and the light source light reflectors 54a and 54b, a device to reflect a laser light is used. For example, a mirror or a prism made of a transparent solid different from air in refractive index, such as glass, crystal or transparent resin, can be used.

A black body 18 to absorb the scattered light traveling in the direction opposite to the light detector 16 may be provided at the terminal end of the observed light path 52. A total reflection mirror 14 may be provided at the terminal end of the light path of the laser light 51.

The shapes of the scattered light reflectors 53a and 53b and the light source light reflectors 54a and 54b in this embodiment can be formed, for example, as described below. In the case where a prism is used, a columnar body having a bottom surface as described below is used. First, rectangular equilateral triangles are arranged so that the hypotenuses are positioned on the same straight line. A rectangle having a side longer than the total length of these hypotenuses is arranged at these hypotenuses so that one end extrudes in the longitudinal direction. When the arrangement is made as stated above, the result becomes like the scattered light reflectors 53a and 53b and the light source light reflectors 54a and 54b shown in FIG. 5.

In the case where a mirror is used, the mirror is used on the lateral surface including two sides, which are equal to each other in length, of the rectangular equilateral triangle of the bottom surface of the foregoing columnar body.

The arrangement of the scattered light reflectors 53a and 53b and the light source light reflectors 54a and 54b in this embodiment can be constructed, for example, as described below. When intervals of reflection points of the observed light path 52 on the reflecting surfaces of the scattered light reflectors 53a and 53b are equal to each other, the width between the reciprocating light paths is made d. The pair of the scattered light reflectors 53a and 53b are arranged to be opposite to each other across the observation area 100, so that the surfaces including the sides opposite to the apexes of the equilateral triangles included on the bottom surfaces, that is, the surfaces without roughness become parallel to each other. At this time, the centers of the pair of the scattered light reflectors 53a and 53b, here, the apexes of the bottom surfaces are positioned to be shifted from each other by d in the length direction of the base of the bottom surface as indicated by alternate long and short dash lines.

Next, the pair of the light source light reflectors 54a and 54b are arranged to be opposite to each other across the observation area 100, so that the surfaces including the sides opposite to the apexes of the equilateral triangles included on the bottom surfaces, that is, the surfaces without roughness become parallel to each other. When intervals of reflection points of the laser light 51 on the reflecting surfaces of the light source light reflectors 54a and 54b are equal to each other, the minimum width between the reciprocating light paths is made d. At this time, the centers of the pair of the light source light reflectors 11, here, the apexes of the bottom surface are arranged to be shifted from each other by d in the length direction of the base of the bottom surface.

Further, the scattered light reflectors 53a and 53b and the light source light reflectors 54a and 54b are arranged so that the laser light 51 intersects the observed light path 52 plural times at different positions. For example, when the light paths of the laser light 51 in the observation area 100 are on the same plane, and the observed light paths 52 in the observation area 100 are on the same plane, the scattered light reflectors 53a and 53b and the light source light reflectors 54a and 54b are arranged so that these planes become the same plane.

Next, the light path of the laser light 51 will be described. The laser light 51 irradiated from the laser light source 12 is incident on the first light source light reflector 54a, is reflected by the reflecting surface of the reflector, passes through the observation area 100, and is incident on the second light source light reflector 54b. The laser light 51 incident on the second light source light reflector 54b is reflected by the reflecting surface of the reflector, passes through the observation area 100, and is again incident on the first light source light reflector 54a. When this is repeated, since the apexes are shifted by d, the incident position of the laser light 51 on the light source light reflectors 54a and 54b is sequentially moved, and finally reaches the total reflection mirror 14. The laser light 51 is reflected by the total reflection mirror 14, and returns along the light path along which it has come. As stated above, the plural light paths of the laser light 51 are produced in the observation area 100.

Next, the observed light path 52 will be described in sequence from the light detector 16. The observed light path 52 passes through the second scattered light reflector 53b, passes through the observation area 100, is incident on the first scattered light reflector 53a, is reflected by the reflecting surface of the reflector, passes through the observation area 100, and is incident on the second scattered light reflector 53b. The observed light path 52 incident on the second scattered light reflector 53b is reflected by the reflecting surface of the reflector, passes through the observation area 100, and is again incident on the first scattered light reflector 53a. When this is repeated, since the apexes are shifted by d, the incident position of the observed light path 52 is sequentially moved, and finally reaches the black body 18. As stated above, the plural light paths of the observed light path are produced in the observation area 100.

Next, the detection of the laser light 51 scattered by a particle will be described. The particle in the observation area 100 scatters the laser light 51. Here, as stated before, the laser light 51 intersects the observed light path 52 plural times at different positions. The scattered light scattered by the particle in the intersection portion travels along the observed light path 52, is condensed by the lens 15, and reaches the light detector 16.

Next, a description will be given to a process of detecting the laser light 51 scattered by a particle from the light incident on the light detector 16. The laser light 51 is modulated and is irradiated to a particle existing in the observation area 100. The laser light 51 scattered by the particle is condensed by the lens 15 and is detected by the light detector 16. Here, the light detected by the light detector 16 includes the laser light 51 scattered by the particle and the other light. The tuned amplifier 62 receives the output of the electric signal obtained by converting the light detected by the light detector 16, and extracts a component synchronous with the modulating signal from the electric signal, and detects the particle.

Next, a tuning signal extraction processing will be described. Although a description will be made while using, as examples, a case (first application example) in which modulation applied to the laser light 51 is a frequency, and a case (second application example) where it is a pulse, a modulation form and an extraction method of a tuning signal is not limited to these.

First Application Example

The modulator 61 generates a modulating signal to cause the frequency of the laser light 51 generated by the laser light source 12 to become a specific frequency, and outputs it to the laser light source 12 and the tuned amplifier 62. This frequency can be arbitrarily set, and can be made, for example, not less than 1 kHz and not higher than 100 kHz.

Figure 7A:
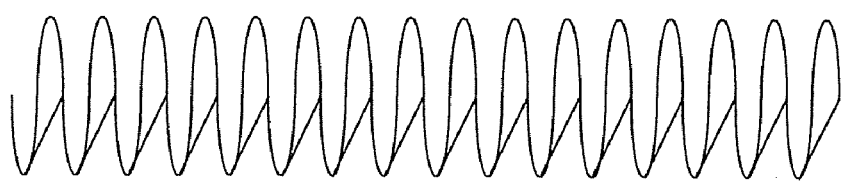
FIG. 7A is a view showing a modulating signal of a modulator in a first application example of the fourth embodiment.

FIG. 7A is a view showing the modulating signal of the modulator 61. The modulated laser light 51 is irradiated to particles existing in the observation area 100.

Figure 7B:
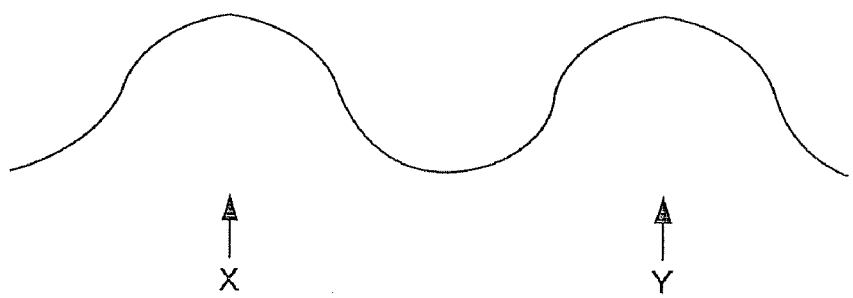
FIG. 7B is a view showing a state in which a laser light scattered by a particle is condensed by a lens, is detected by a light detector and is converted into an electric signal.

FIG. 7B is a view showing a state where the laser light 51 scattered by the particle is condensed by the lens 15, is detected by the light detector 16, and is converted into an electric signal. Here, it is assumed that the laser light 51 scattered by the particle is not included in a portion X and is included in a portion Y.

The signal outputted from the light detector 16 is inputted to the tuned amplifier 62. The tuned amplifier 62 includes an amplifying circuit to amplify the signal, and a band-pass filter to cause only a signal synchronous with the modulating signal inputted from the modulator 61 to pass through.

Figure 7C:
FIG. 7C is a view showing an output signal from a tuned amplifier.

FIG. 7C is a view showing the output signal from the tuned amplifier 62. As described above, from the laser light 51 scattered by the particle and the other light, only the former is extracted by the band-pass filter and the particle is detected by this, Second Application Example The modulator 61 generates a modulating signal to cause the pulse of the laser light 51 generated by the laser light source 12 to become a definite periodic or random pulse, and outputs it to the laser light source 12 and the tuned amplifier 62.

Figure 8A:
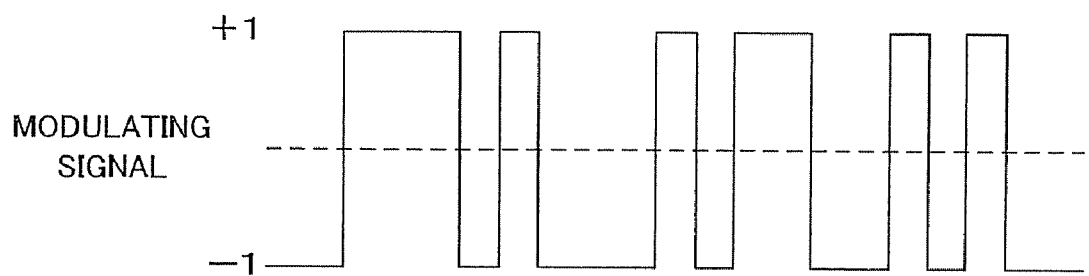
FIG. 8A is a view showing a modulating signal of a modulator of a second application example of the fourth embodiment.

FIG. 8A is a view showing the modulating signal of the modulator 61. The modulated laser light 51 is irradiated to particles existing in the observation area 100. For example, it is assumed that +1 denotes that the laser light is irradiated, and −1 denotes that it is not irradiated.

Figure 8B:
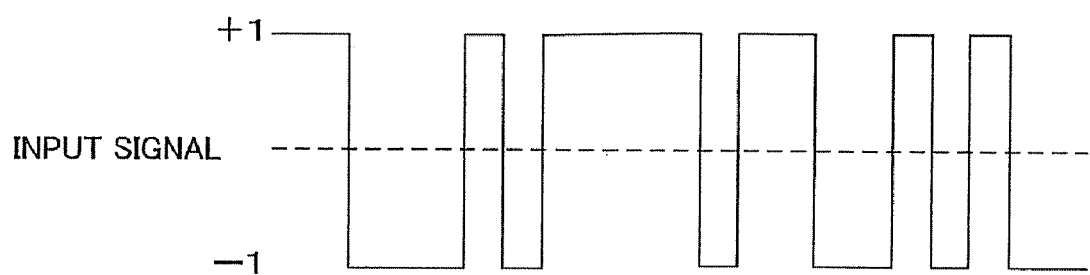
FIG. 8B is a view showing a state in which a laser light scattered by a particle is condensed by a lens, is detected by a light detector and is converted into an electric signal.

FIG. 8B is a view showing a state in which the laser light 51 scattered by the particle is condensed by the lens 15, is detected by the light detector 16, and is converted into an electric signal.

The signal outputted from this light detector 16 is inputted to the tuned amplifier 62. The tuned amplifier 62 includes an amplifying circuit to amplify a signal, an A/D converter to convert analog data into digital data, and an integrating device to integrate a modulating signal inputted from the modulator 61 and an output signal inputted from the light detector 16. The A/D converter outputs, for example, +1 when detecting a light, and −1 when not detecting.

The integrating device outputs +1 when the modulating signal is +1 and the output signal is +1, and the modulating signal is −1 and the output signal is −1, that is, outputs +1 in the case where the modulating signal and the output signal are coincident with each other, and outputs −1 when not so.

Figure 8C:
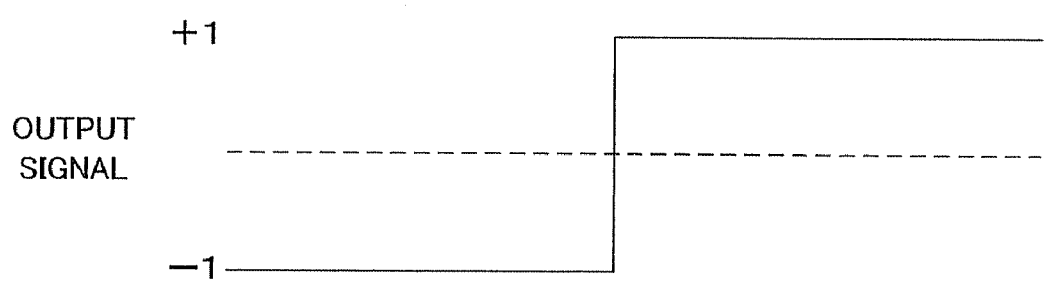
FIG. 8C is a view showing an output signal from a tuned amplifier.

FIG. 8C is a view showing the output signal from the tuned amplifier 62. As stated above, from the laser light 51 scattered by the particle and the other light, only the former is extracted by the integrating device, and the particle is detected by this.

Incidentally, FIG. 8B and FIG. 8C show the theoretical patterns for explanation. In actual measurement, in the case where the laser light 51 scattered by the particle is not included, the integrated value by the integrating device becomes zero when it is averaged. Thus, the particle can be detected by calculating the average of the integrated value.

As described above, in this embodiment, the laser light 51 is modulated, and the light synchronous with the modulation added to the laser light 51, that is, the laser light 51 scattered by the particle is detected from the light incident on the light detector 16, and therefore, even if a light other than the laser light 51 exists in the observation area 100, the particle is detected. By this, there is an effect that the particle can be detected even if a light other than the laser light 51 exists in the observation area 100.

Fifth Embodiment

Next, a fifth embodiment will be described. This embodiment is characterized in that an irradiation area of a laser light is widened in the first to the fourth embodiments. Hereinafter, an example in which the irradiation area is widened will be described.

Figure 9A:
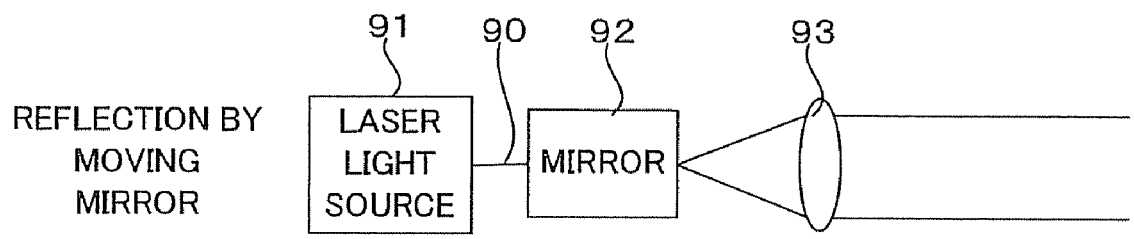
FIG. 9A is a view showing an example in which a laser light is reflected by a moving mirror in a light path changing method of a fifth embodiment.

FIG. 9A is a view showing an example in which a laser light 90 is reflected by a moving mirror. The laser light 90 irradiated from a laser light source 91 is reflected by a mirror 92 making a motion such as rotation or vibration, and the light path of the laser light 90 is changed to be, for example, radial. The laser light 90 changed to be radial is changed into a parallel light path by a lens 93, and is irradiated to the observation area 100.

Figure 9B:
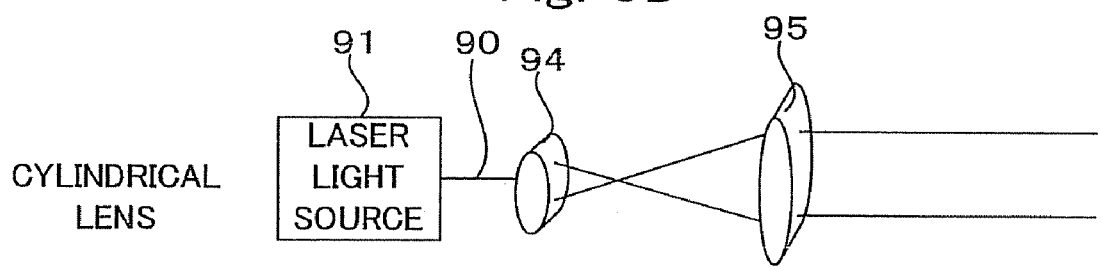
FIG. 9B is a view showing an example in which a cylindrical lens is used in the light path changing method of the fifth embodiment.

FIG. 9B is a view showing an example using a cylindrical lens 94. The cylindrical lens is a lens to refract a light in one direction, and for example, a columnar one can be used.

A laser light 90 irradiated from a laser light source 91 is incident on the first cylindrical lens 94, and the section of the laser light 90 is changed to become long in one direction. The laser light 90 changed to become long in the one direction is changed into a parallel light path by a cylindrical lens 95, and is irradiated to the observation area 100.

Figure 9C:
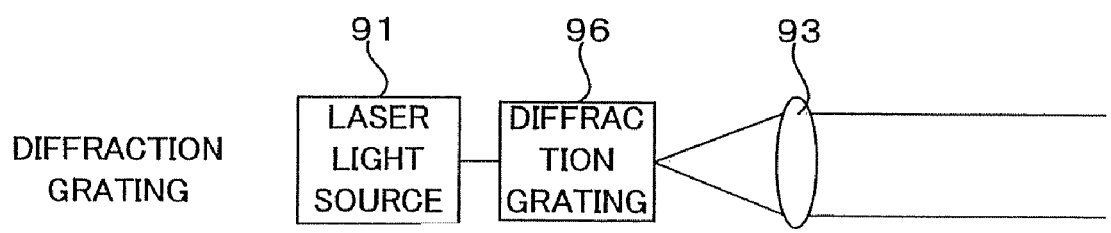
FIG. 9C is a view showing an example in which a diffraction grating 96 is used in the light path changing method of the fifth embodiment.

FIG. 9C is a view showing an example using a diffraction grating 96. The diffraction grating is an optical element having a minute slit and when a laser light passes through the slit, the diffraction occurs.

A laser light 90 irradiated from a laser light source 91 is incident on the diffraction grating 96, and the laser light 90 is changed to become radial. The laser light 90 changed to become radial is changed into a parallel light path by a lens 93, and is irradiates to the observation area 100.

As described above, in this embodiment, the irradiation area of the laser light is widened. By this, since the laser light can be irradiated to more particles, there is an effect that the detection accuracy of particles can be further increased.

Sixth Embodiment

Next, a sixth embodiment will be described. This embodiment is characterized in that a light source light reflector and a scattered light reflector are integrally formed in the first to the fifth embodiments.

Figure 10:
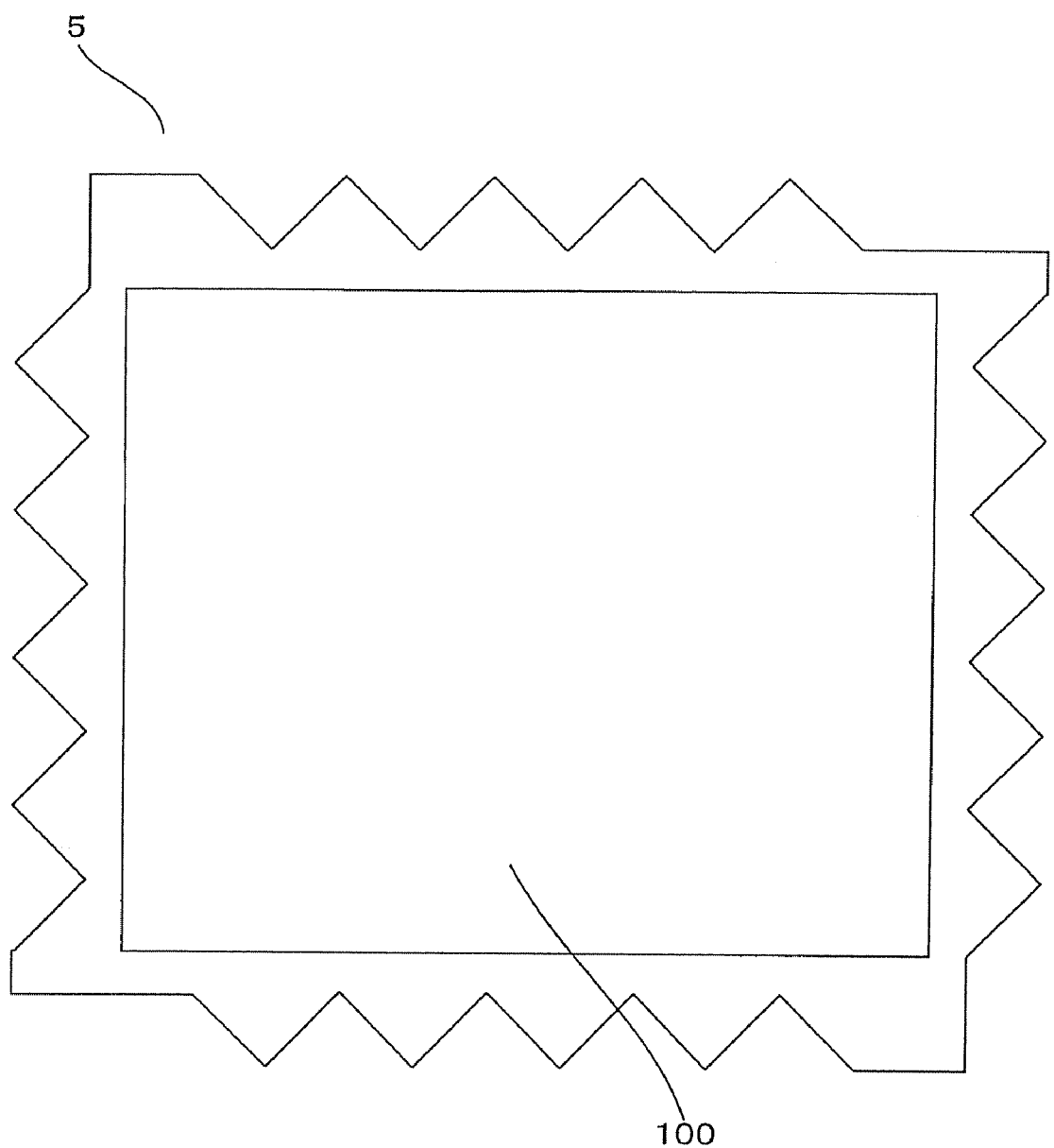
FIG. 10 is a view showing a structural example of a reflector of a sixth embodiment.

A reflector 5 shown in FIG. 10 is an example in which a light source light reflector and a scattered light reflector are integrally formed. The ends of the light source light reflector and the scattered light reflector are alternately coupled so that the laser light intersects the observed light path plural times at different positions, and they are integrally formed to surround the observation area 100.

As a result that the reflector 5 is integrally formed, the section of the observation area 100 is square, however, it may be triangular or polygonal.

As described above, in this embodiment, the light source light reflector and the scattered light reflector are integrally formed. By this, there is an effect that the manufacture cost can be reduced.

<Image Forming Apparatus>

Next, an image forming apparatus will be described.

Figure 11:
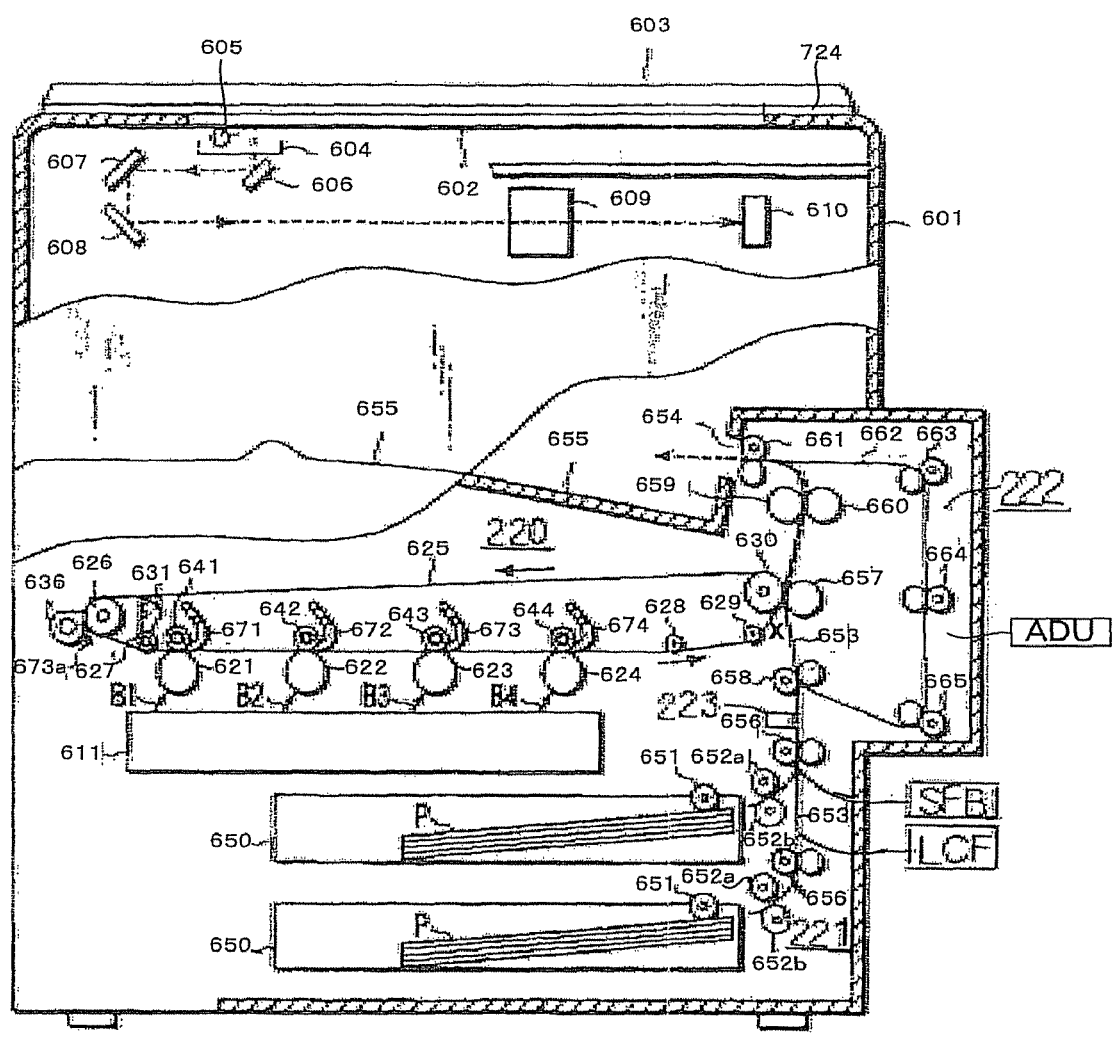
FIG. 11 is a view showing a structural example of an image forming apparatus.

FIG. 11 is a view showing a structural example of the image forming apparatus. As shown in FIG. 11, a document stand 602 for mounting documents, which is formed of a transparent material such as, for example, a glass plate, is provided at an upper part of an apparatus main body 601. A cover 603 is openably and closably mounted on the apparatus main body 601 so as to cover the document stand 602.

A scan unit (not shown) to optically read an image of an original document mounted on the document stand 602 is provided at the lower side of the document stand 602 in the inside of the apparatus main body 601. For example, the scan unit includes a carriage 604, reflecting mirrors 606, 607 and 608 to reflect a light of an exposure lamp 605 reflected by the original document, a scaling lens block 609 to scale the reflected light, and a CCD (Charge Coupled Device) 610. The carriage 604 is provided with the exposure lamp 605 to irradiate the light to the document stand 602, and is constructed to be capable of reciprocating along the lower surface of the document stand 602.

The carriage 604 moves while the exposure lamp 605 is being turned on, so that the original document mounted on the document stand 602 is exposed. A reflected light image of the original document, which is mounted on the document stand 602, by the exposure is projected onto the CCD 610 through the reflecting mirrors 606, 607 and 608 and the scaling lens block 609. The CCD 610 outputs image data corresponding to the projected reflected light image of the original document.

An image forming unit 220 is provided below the scan unit in the inside of the apparatus main body 601. The image forming unit 220 includes, for example, a print engine (not shown) and a process unit (not shown).

The print engine includes an exposure unit 611. The process unit includes photoconductive drums 621, 622, 623 and 624 arranged along the exposure unit 611, an endless transfer belt 625 arranged to be opposite to the exposure unit 611 across the photoconductive drums 621, 622, 623 and 624, a drive roller 626 to drive the transfer belt 625, primary transfer rollers 641, 642, 643 and 644 arranged to be opposite to the photoconductive drums 621, 622, 623 and 624 across the transfer belt 625, and a transfer roller drive unit to drive the primary transfer rollers 641, 642, 643 and 644.

The transfer belt 625 is stretched over the drive roller 626, guide rollers 627, 628 and 629 and a driven roller 630, receives power from the drive roller 626 and rotates and runs in the counterclockwise direction. The guide roller 627 is provided to be freely moved up and down, and receives the rotation of a cam 631 to be moved to the transfer belt 625 side. By this, the guide roller 627 displaces the transfer belt 625 to the side of the photoconductive drums 621, 622, 623 and 624.

The image forming unit 220 executes an image formation process to form an image based on image data (image signal outputted from the CCD 610) and to print the image onto the record medium being conveyed. That is, after the image signal outputted from the CCD 610 is suitably processed, it is supplied to the exposure unit 611. The exposure unit 611 emits a laser beam B1 corresponding to a yellow color image signal to the photoconductive drum 621 for yellow, emits a laser beam B2 corresponding to a magenta color image signal to the photoconductive drum 622 for magenta, emits a laser beam B3 corresponding to a cyan color image signal to the photoconductive drum 623 for cyan, and emits a laser beam B4 corresponding to a black color image signal to the photoconductive drum 624 for black.

The primary transfer rollers 641, 642, 643 and 644 are moved (lowered) to the transfer belt 625 side, so that the transfer belt 625 is brought into contact with the photoconductive drums 621, 622, 623 and 624, and visible images on the photoconductive drums 621, 622, 623 and 624 are transferred to the transfer belt 625.

A not-shown drum cleaner, a charge-removal lamp, a charging unit, and a developing unit are sequentially arranged around the photoconductive drum 621. The drum cleaner includes a drum cleaning blade which comes in contact with the surface of the photoconductive drum 621, and scrapes away a developer remaining on the surface of the photoconductive drum 621 by the drum cleaning blade.

The charge-removal lamp removes a charge remaining on the surface of the photoconductive drum 621. The charging unit applies a high voltage to the photoconductive drum 621, so that the surface of the photoconductive drum 621 is charged with an electrostatic charge. The laser beam B1 emitted from the exposure unit 611 is irradiated to the surface of the charged photoconductive drum 621. An electrostatic latent image is formed on the surface of the photoconductive drum 621 by this irradiation. The developing unit supplies a yellow developer (toner) to the surface of the photoconductive drum 621, so that the electrostatic latent image on the surface of the photoconductive drum 621 is made a visible image.

Also in the other photoconductive drums 622, 623 and 624, similarly, developers of the corresponding colors are used and electrostatic latent images on the surfaces of the respective photoconductive drums 622, 623 and 624 are made visible images.

A cleaner 636 is provided at a position opposite to the drive roller 626 of the image forming unit 220 across the transfer belt 625. This cleaner 636 includes a cleaning blade 636a which comes in contact with the transfer belt 625, and scrapes away a developer remaining on the transfer belt 625 by the cleaning blade 636a.

The printing mode is changed as described below. Hooks 671, 672, 673 and 674 are provided in the vicinities of the primary transfer rollers 641, 642, 643 and 644. The hooks 671, 672, 673 and 674 are engaged with shafts of the primary transfer rollers 641, 642, 643 and 644 to raise the shafts while rotating, and move the primary transfer rollers 641, 642, 643 and 644 in the direction of separating from the photoconductive drums 621, 622, 623 and 624. The printing mode, such as a full-color mode, all separation mode or a monochrome mode, is changed by not moving any of the primary transfer rollers 641, 642, 643 and 644 or by moving them and changing the combination.

Next, a containing mechanism and a supply mechanism of record media will be described. Plural record medium cassettes 650 to contain record media are provided below the exposure unit 611. In these record medium cassettes 650, a number of record media P different from one another in record medium type are contained in a stacked state. A record medium supply mechanism 221 to supply the record medium in the record medium cassette 650 one by one from above is provided at an exit portion (right in the drawing) of each of the record medium cassettes 650. By this record medium supply mechanism 221, the record medium P is taken out one by one from any one of the record medium cassettes 650. The record medium supply mechanism 221 for taking out includes a pickup roller 651, a record medium supply roller 652a, and a separating roller 652b, separates the record medium P, which is taken out from the record medium cassette 650, one by one, and supplies it to a record medium conveyance path 653.

Next, the conveyance path of the record medium will be described. The record medium conveyance path 653 extends to an upper record medium discharge port 654 through the driven roller 630 of the image forming unit 220. The record medium discharge port 654 faces a record medium discharge unit 655 continuous with the outer peripheral surface of the apparatus main body 601. At the starting end side of the conveyance path 653, a conveyance roller 656 is provided in the vicinity of each of the record medium supply mechanisms 221. When the record medium is supplied by one of the record medium supply mechanisms 221, the record medium conveyance path 653 conveys the supplied record medium to the record medium discharge unit 655.

A secondary transfer roller 657 is provided at a halfway position of the record medium conveyance path 653 where it is opposite to the driven roller 630 across the transfer belt 625. A register roller 658 is provided at an upstream position of the driven roller 630 and the secondary transfer roller 657 in the conveyance direction.

At the timing in synchronization with the transfer operation as an operation of transferring an image formed with a developer (toner) to the record medium by the transfer belt 625 and the secondary transfer roller 657, the register roller 658 sends the record medium P to between the transfer belt 625 and the secondary transfer roller 657. The secondary transfer roller 657 holds the record medium P sent from the register roller 658 between itself and the transfer belt 625 on the driven roller 630, transfers the visible image formed with the developer (toner) and transferred on the transfer belt 625 to this record medium P, and prints it. As stated above, the register roller 658 conveys the record medium P to the image forming unit 220 including the transfer belt 625 and the secondary transfer roller 657 in synchronization with the transfer operation of the image forming unit 220.

A heat roller 659 for heat fixation and a press roller 660 in contact with the heat roller 659 are provided at a downstream position of the record medium conveyance path 653 with respect to the secondary transfer roller 657. The image transferred on the record medium P is fixed by the heat roller 659 and the press roller 660. Incidentally, a record medium discharge roller 661 is provided at the terminal end of the record medium conveyance path 653.

An auto duplex unit (hereinafter referred to as ADU) 222 may be provided in the apparatus main body 601. The ADU 222 is installed so as to couple a sub-conveyance path 662, which is a path for conveying the record medium P in the ADU 222, to the terminal end of the record medium conveyance path 653 and to an inlet toward the register roller 658. The sub-conveyance path 662 branches away from the downstream side (terminal end of the record medium conveyance path 653) of the record medium conveyance path 653 with respect to the image forming unit 220, and meets the upstream side (upstream side position of the register roller 658) of the record medium conveyance path 653 with respect to the image forming unit 220.

The sub-conveyance path 662 reverses the obverse and reverse of the record medium P for two-sided printing. The sub-conveyance path 662 is provided with record medium supply rollers 663, 664 and 665, and the ADU 222 reversely sends the record medium P conveyed from the image forming unit 220 to the record medium discharge unit 655, conveys it along the sub-conveyance path 662, and causes it to meet the record medium conveyance path 653 at the upstream side of the image forming unit 220. When the conveyance is made in this way, the obverse and reverse of the record medium P is reversed.

After the record medium P returned to the upstream side of the image forming unit 220 through the sub-conveyance path 662 meets the record medium conveyance path 653, the register roller 658 establishes synchronization with the transfer operation of the image forming unit 220, and the record medium is sent to the transfer position where the transfer belt 625 is in contact with the secondary transfer roller 657. In this way, the visible image on the transfer belt 625 is transferred also to the reverse surface of the record medium P and is printed.

When the two-sided printing is specified through the operation panel 724 provided on the apparatus main body 601 or the computer connected to the apparatus main body 601 through the network, the sub-conveyance path 662 of the ADU 222 is brought into the state of performing the operation to reverse the obverse and reverse of the record medium P.

Next, an additionally provided device will be described. In the example of the apparatus main body 601 shown in FIG. 11, the two record medium cassettes 650 are provided as the supply source of the record medium. Three or more record medium cassettes 650 may be provided in the apparatus main body 601. In addition, although not shown, a manual feed record medium supply mechanism (hereinafter referred to as SFB), or a large capacity record medium feeder (hereinafter referred to as LCF), which is a record medium supply mechanism capable of containing several thousand record media in a stacked form, can also be provided. The SFB or the LCF is installed in the apparatus main body 601 so that the path to supply the record medium meets the record medium conveyance path 653.

A record medium kind sensor 223 may be provided in the apparatus main body 601. The record medium kind sensor 223 is arranged on the upstream side of the record medium conveyance path 653 with respect to the image forming unit 220 and at an upstream position with respect to the register roller 658, and detects the record medium kind of the record medium P conveyed through the record medium conveyance path 653. As the record medium kind sensor 223, for example, a well-known sensor to determine the kind of the record medium P by detecting the thickness of the record medium P or the light transmittance can be used.

In the case where the SFB or the LCF is installed, the record medium kind sensor 223 is arranged on the downstream side of the meeting point between the record medium supply path from the SFB and the LCF and the record medium conveyance path 653. When the arrangement is made as stated above, the one record medium kind sensor 223 can detect the kinds of the record media P conveyed on the record medium conveyance path 653 from all record medium supply sources.

Next, installation positions of the particle detecting device 1, 2, 3 or 4 will be described. It is desirable that the particle detecting device 1, 2, 3 or 4 of each embodiment is installed on the side of the printed surface of the record medium P by the image forming unit 220.

Besides, it is further desirable that the particle detecting device 1, 2, 3 or 4 of each embodiment is installed in an area X which is positioned in the vicinity of the upstream side of the record medium conveyance path 653 with respect to a position where the transfer belt 625 and the record medium P conveyed through the record medium conveyance path 653 are held between the secondary transfer roller 657 and the driven roller 630, is on the side of the surface of the transfer belt 625 to which the developer (toner) is attached, and is on the side of the printed surface of the record medium P conveyed through the record medium conveyance path 653.

FIG. 11 shows an example of the area X. A particle such as paper powder existing in this area X is liable to be sucked in between the developer of the transfer belt 625 and the printed surface of the record medium P. When the particle is sucked to the printed surface, it is attached to an image formed on the record medium P, and deteriorates the picture quality. That is, this area X is a position where the particle most exerts a bad influence on the picture quality of an image formed on the record medium P, and it is most effective to reduce the particle in this area X in order to form an excellent image on the record medium. Accordingly, it is desirable that the particle detecting device 1, 2, 3 or 4 of each embodiment is installed in this area X.

Incidentally, the particle detecting device 1, 2, 3 or 4 can also be additionally provided with an alarm device. The alarm device receives data of the detection amount of particle (number of particles) detected by the particle detecting device 1, 2, 3 or 4 at specified time intervals, determines whether it reaches a previously determined threshold value, for example, a maximum value of the allowable number of particles determined according to the transfer accuracy of each device, and gives an alarm in a case where it is determined that the data reaches the threshold value. The alarm may be issued by the alarm device itself using sound or light, or an alarm signal may be outputted to a control unit of the image forming apparatus. By this, when the number of particles, such as powders of the record medium, reaches the value having an influence on the transfer of the developer (toner) to the record medium P, the alarm is given to the user so that the maintenance is performed.

As described above, the particle detecting device 1, 2, 3 or 4 is installed in the vicinity of the upstream side of the record medium conveyance path 653 with respect to the position where the transfer belt 625 of the apparatus main body 601 and the record medium P conveyed through the record medium conveyance path 653 are held between the secondary transfer roller 657 and the driven roller 630. By this, there is an effect that it becomes possible to efficiently perform the detection of the particle having a bad influence on the picture quality.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A particle detecting device comprising:
a laser light source to irradiate a laser light;
a moving mirror to widen an irradiation range of the laser light by reflection, a lens to widen it by refraction or a diffraction grating to widen it by diffraction;
a light detector to detect the laser light scattered by a particle; and
one of or both of a light source light reflector to reflect the laser light to make it intersect an observed light path of the light detector plural times at different positions, and a scattered light reflector to reflect the observed light path of the light detector to make it intersect the laser light plural times at different positions.

2. A particle detecting device comprising:
a laser light source to irradiate a laser light;
a light detector to detect the laser light scattered by a particle; and
one of or both of a light source light reflector that is a columnar body having a triangular or polygonal bottom surface and reflects the laser light to make it intersect an observed light path of the light detector plural times at different positions, and
a scattered light reflector that is a columnar body having a triangular or polygonal bottom surface and reflects the observed light path of the light detector to make it intersect the laser light plural times at different positions.

3. The particle detecting device according to claim 1, wherein the particle detecting device further comprises:
a modulator to modulate the laser light; and
a tuned amplifier to extract a signal synchronous with the modulating signal of the modulator from an output signal obtained by converting the light detected by the light detector and outputting it.

4. The particle detecting device according to claim 2, wherein the particle detecting device further comprises:
a modulator to modulate the laser light; and
a tuned amplifier to extract a signal synchronous with the modulating signal of the modulator from an output signal obtained by converting the light detected by the light detector and outputting it.

5. The particle detecting device according to claim 1, wherein
a pair of light source light reflectors are arranged to be opposite to each other and reflect the laser light to make it intersect an observed light path of the light detector plural times at different positions, and
a pair of scattered light reflectors are arranged to be opposite to each other and reflect the observed light path of the light detector to make it intersect the laser light plural times at different positions.

6. The particle detecting device according to claim 2, wherein
a pair of light source light reflectors are arranged to be opposite to each other and reflect the laser light to make it intersect an observed light path of the light detector plural times at different positions, and
a pair of scattered light reflectors are arranged to be opposite to each other and reflect the observed light path of the light detector to make it intersect the laser light plural times at different positions.

7. The particle detecting device according to claim 1, wherein
a pair of the light source light reflectors are arranged to be opposite to each other while centers are shifted from each other by a specific distance, and reflect the laser light to make it intersect an observed light path of the light detector plural times at different positions, and
a pair of the scattered light reflectors are arranged to be opposite to each other while centers are shifted from each other by a specific distance, and reflect the observed light path of the light detector to make it intersect the laser light plural times at different positions.

8. The particle detecting device according to claim 2, wherein
a pair of the light source light reflectors are arranged to be opposite to each other while centers are shifted from each other by a specific distance, and reflect the laser light to make it intersect an observed light path of the light detector plural times at different positions, and
a pair of the scattered light reflectors are arranged to be opposite to each other while centers are shifted from each other by a specific distance, and reflect the observed light path of the light detector to make it intersect the laser light plural times at different positions.

9. The particle detecting device according to claim 1, wherein
a pair of the light source light reflectors are formed of a mirror or a transparent solid different from air in refractive index, and reflects the laser light to make it intersect an observed light path of the light detector plural times at different positions; and a pair of the scattered light reflectors are formed of mirror or transparent solids different from air in refractive index, are arranged to be opposite each other, and reflect the observed light path of the light detector to make it intersect the laser light plural times at different positions.

10. The particle detecting device according to claim 2, wherein
- a pair of the light source light reflectors are formed of a mirror or a transparent solid different from air in refractive index, and reflects the laser light to make it intersect an observed light path of the light detector plural times at different positions; and
- a pair of the scattered light reflectors are formed of mirror or transparent solids different from air in refractive index, are arranged to be opposite each other, and reflect the observed light path of the light detector to make it intersect the laser light plural times at different positions.

11. The particle detecting device according to claim 1, wherein
the light source light reflector and the scattered light reflector are integrally formed.

12. The particle detecting device according to claim 2, wherein
the light source light reflector and the scattered light reflector are integrally formed.

13. The particle detecting device according to claim 1, wherein
The particle detecting device is installed in an image forming apparatus, and the light detector detects the laser light scattered by a paper particle.

14. The particle detecting device according to claim 2, wherein
The particle detecting device is installed in an image forming apparatus, and the light detector detects the laser light scattered by a paper particle.

* * * * *